United States Patent
Liu et al.

(10) Patent No.: US 10,093,883 B2
(45) Date of Patent: Oct. 9, 2018

(54) GLUCOSE GEMINI SURFACTANT COMPOUND AND METHOD FOR PREPARATION THEREOF

(71) Applicant: ZHEJIANG UNIVERSITY, Hangzhou, Zhejiang Province (CN)

(72) Inventors: Songbai Liu, Hangzhou (CN); Jin Feng, Hangzhou (CN)

(73) Assignee: ZHEJIANG UNIVERSITY, Hangzhou (CN)

(*) Notice: Subject to any disclaimer, the term of this patent is extended or adjusted under 35 U.S.C. 154(b) by 8 days.

(21) Appl. No.: 15/516,008

(22) PCT Filed: Nov. 10, 2014

(86) PCT No.: PCT/CN2014/090672
§ 371 (c)(1),
(2) Date: Mar. 30, 2017

(87) PCT Pub. No.: WO2016/049967
PCT Pub. Date: Apr. 7, 2016

(65) Prior Publication Data
US 2017/0292087 A1    Oct. 12, 2017

(30) Foreign Application Priority Data

Sep. 30, 2014  (CN) .......................... 2014 1 0519634
Sep. 30, 2014  (CN) .......................... 2014 1 0521042

(51) Int. Cl.
C11D 1/83       (2006.01)
C11D 1/66       (2006.01)
C11D 3/22       (2006.01)

(52) U.S. Cl.
CPC ............... *C11D 1/83* (2013.01); *C11D 1/662* (2013.01); *C11D 3/222* (2013.01)

(58) Field of Classification Search
CPC ............ C11D 1/83; C11D 1/662; C11D 3/222
See application file for complete search history.

(56) References Cited

FOREIGN PATENT DOCUMENTS

| CN | 102895914 A | 1/2013 | |
| CN | 102895914   | * 3/2014 | .............. B01F 17/56 |
| CN | 102895915 A | 1/2017 | |

OTHER PUBLICATIONS

Liu et al., "A Novel Type of Highly Effective Nonionic Gemini Alkyl O-Glucoside Surfactants: A Versatile Strategy of Design", Langmuir, No. 27, vol. 19, Jun. 19, 2013, pp. 8511-8516.

* cited by examiner

Primary Examiner — Brian P Mruk
(74) Attorney, Agent, or Firm — Jiwen Chen

(57) ABSTRACT

The present invention discloses a glucose gemini surfactant compound comprising a dodecyl glucose gemini surfactant and tetradecyltrimethylammonium chloride, or a tetradecyl glucose gemini surfactant and cetyl trimethylammonium bromide; the present invention also discloses a process for the preparation of the glucose gemini surfactant compounds. The glucose gemini surfactant compounds of the invention have the high activity characteristic of the gemini surfactant and is suitable for the separation and extraction of the detergents and the biofilm protein, and are novel non-toxic or low toxic and biodegradable glycosyl gemini surfactants. The preparation method of the compound surfactants is simple and easy to be industrialized.

10 Claims, No Drawings

GLUCOSE GEMINI SURFACTANT COMPOUND AND METHOD FOR PREPARATION THEREOF

This is a U.S. national stage application of PCT Application No. PCT/CN2014/090672 under 35 U.S.C. 371, filed Nov. 10, 2014 in Chinese, claiming the priority of Chinese Patent Application No. 201410521042.X filed Sep. 30, 2014 and Chinese Patent Application No. 201410519634.8 filed Sep. 30, 2014, which are hereby incorporated by reference.

TECHNICAL FIELD

The present invention relates to the field of surfactant preparation, and more particularly to a glucose gemini surfactant compound and a process for its preparation.

BACKGROUND TECHNIQUE

The industry of surfactants and synthetic detergents dates back to the 1930s. Synthetic surfactants and detergents derived from petrochemical raw materials have broken the dominance of soaps, and the current research interests of surfactants are alkyl epoxy carboxylates (AEC), gemini surfactants, AB type block polymer surfactants, bola type surfactants, dendrimer type surfactants, low foaming or foamless surfactants. With the continuous improvement of the people's living standards and environmental awareness, the traditional commercial surfactant has been unable to meet the requirements of surfactant safety, environmental protection and low cost, and it is being gradually eliminated, replaced by a new type of green surfactant. So green surfactants such as gemini surfactants have been favored by scientists around the world and have set off a new research boom.

Gemini surfactants comprises two or more of the same or almost identical surfactant monomers connected by chemical bonds where the amphiphilic components are linked together via the hydrophilic head groups or near the hydrophilic head groups. These surfactants include anionic, non-ionic, cationic, zwitterionic, anionic-nonionic and cationic-nonionic types. The special structures of gemini surfactants determine that they have better performance than conventional surfactants. Usually, they have two hydrophilic groups and hydrophobic groups connected through the linking chain. The connection by a chemical bond reduces the electrostatic repulsion between the polar groups and the force between the hydration layers, and so endows the gemini surfactant extremely low cmc (critical micelle concentration). At the same time, due to the compact symmetrical structure the gemini surfactant molecules have special self-assembly behavior and excellent ability to reduce the surface tension of the aqueous solution, so that they are widely used in detergents and cosmetics industries, the fields of petroleum, coal, mining, textile, medicine and other industries and agriculture.

The patent literature (Application Serial No: CN201010532886.6) discloses a gemini surfactant and a process for the preparation thereof. The structure of the gemini surfactant is shown in formula (I).

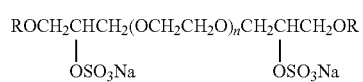

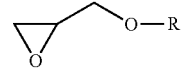

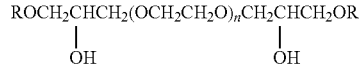

Wherein: R is selected from the group consisting of C8-C16 alkyl; n is a natural number from 1 to 3, and a process for the preparation of a cationic gemini surfactant represented by the formula (I) in the literature, comprising the steps of: 1) C8-C16 fatty alcohols and epichlorohydrin are reacted in the presence of a basic compound and a phase transfer catalyst to form a compound of the formula (II) wherein R is as defined in formula (I); 2) the compound represented by the formula (II) and the polyethylene glycol are reacted in the presence of an alkali metal and are acidified to give a compound of the formula (III), wherein the degree of polymerization of the polyethylene glycol is from 1 to 3; 3) the compound represented by the formula (III) is reacted with chlorosulfonic acid and is alkalized to give a gemini surfactant represented by the formula (I). The surfactants provided by the above documents have good temperature resistance, salt resistance, foaming property, emulsifying property and good synergistic effect with other types of surfactants. However, the instability, strong volatility and potential carcinogenic toxicity of epichlorohydrin results in high preparative cost of the above-mentioned gemini surfactants and limits their further industrialization produce.

Highly active dodecyl and tetradecyl glucose gemini surfactants (Patent Publication No. CN102895914A; Patent Publication No. CN102895915A) have been developed in our lab. Further improvement of the surface activity through combination with other surfactants is an effective way to optimize surface activity, which can greatly reduce the cost of research and industrial application.

THE SUMMARY OF THE INVENTION

The present invention provides a compound of dodecyl glucose gemini surfactant with tetradecyltrimethylammonium chloride, or tetradecyl glucose gemini surfactant and cetyltrimethylammonium bromide, and realizes effective optimization of the dodecyl glucose gemini surfactant or cetyltrimethylammonium bromide compound surface activity, which is suitable for detergents and biofilm protein separation and extraction, and is a novel non-toxic, biologically degradable type of green gemini surfactant compound.

The present invention also provides a preparative method for the compound of a dodecyl glucose gemini surfactant and tetradecyltrimethylammonium chloride, or a tetradecyl glucose gemini surfactant with cetyltrimethylammonium bromide compound, which has the advantage of simple operation and is suitable for industrial production.

A dodecyl glucose gemini surfactant compound comprises a dodecyl glucose gemini surfactant and tetradecyltrimethylammonium chloride; the structure of the dodecyl glucose gemini surfactant is represented by the following formula.

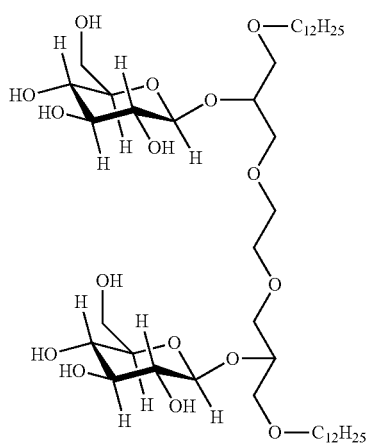

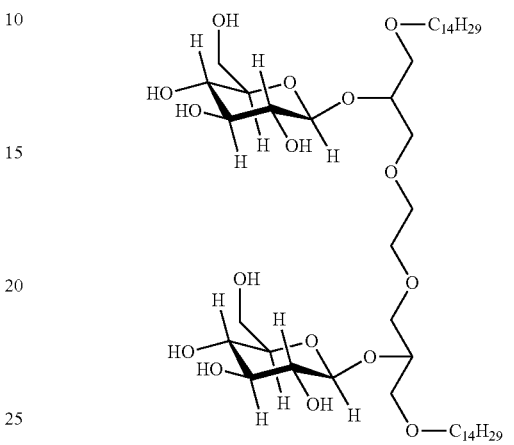

Preferably, the molar ratio of dodecyl glucose gemini surfactant to tetradecyltrimethylammonium chloride is from 1.5 to 2.5:1, more preferably in a molar ratio of 2:1; experiments show that the dodecyl glucose gemini surfactant with other common surfactants has no such surface activity promotion effect, indicating that the dodecyl glucose gemini surfactant and tetradecyl trimethyl ammonium chloride molecules have a specific interaction between the molecules. In particular, when the molar ratio of the two is 2:1, the surface activity of the compound is 3 times higher than that of the dodecyl glucose gemini surfactant.

The above dodecyl glucose gemini surfactant and tetradecyltrimethylammonium chloride compound product can be stored in the form of a solid or in the form of a solution; when stored in a solution, the solvent used may be water or alcohol solvents, ketone solvents and the like; as preferred, the solvent includes one or more of water, methanol, ethanol and acetone.

The present invention also provides a process for the preparation of a compound of dodecyl glucose gemini surfactant and tetradecyltrimethylammonium chloride as follows:

The dodecyl glucose gemini surfactant and tetradecyl trimethyl ammonium chloride are dissolved in a certain amount of solvent, respectively. A certain amount of tetradecyl trimethyl ammonium chloride solution and dodecyl glucose gemini surfactant solution is mixed to obtain the compound. The solvent is water and an organic solvent, and the organic solvent is an alcoholic solvent such as ethanol and methanol, a ketone solvent such as acetone. The prepared product may be in the form of a solution or dried as a solid powder.

The dodecyl glucose gemini surfactant and tetradecyltrimethylammonium chloride used in the present invention are all existing compounds that are commercially available or can be prepared by the available method. The present invention is carried out at room temperature unless otherwise specified.

In the above production method, the molar ratio of the dodecyl glucose gemini surfactant to tetradecyltrimethylammonium chloride is 1.5 to 2.5:1. As preferred, the molar ratio of the dodecyl glucose gemini surfactant to tetradecyltrimethylammonium chloride is 2:1. When the technical scheme is adopted, the prepared surfactant has better performance and is three times of the activity of the dodecyl glucose gemini surfactant. In the present invention, trimethyl tetradecylammonium chloride itself has excellent emulsifying property, antistatic property, bactericidal property, and disinfectability.

A tetradecyl glucose gemini surfactant compound comprises a tetradecylglucose gemini surfactant and cetyltrimethylammonium bromide; the structure of the tetradecylglucose gemini surfactant is shown as follows.

Preferably, the molar ratio of tetradecyl glucose gemini surfactant to cetyltrimethylammonium bromide is from 3.5 to 4.5:1, more preferably in a molar ratio of 4:1. Experiments show that the tetradecyl gemini surfactant with other common surfactants has no such surface activity promotion effect, indicating that the tetradecyl gemini surfactant and cetyltrimethylammonium bromide molecules have the specific interaction. In particular, when the molar ratio is chosen to be 4:1, the compound increased the surface activity by ten times than that of the tetradecyl glucose gemini surfactant.

The compound of the present invention may be stored in solid form or in the form of a solution; when stored as a solution, the solvent may be at least one selected from the group consisting of water, an alcoholic solvent, and a ketone solvent; preferably, the solvent includes water, methanol, ethanol, or acetone.

The present invention also provides a process for the preparation of the tetradecyl glucose gemini surfactant compound comprising the steps of: dissolving tetradecyl glucose gemini surfactant and cetyltrimethylammonium bromide into a quantity of solvent, and then a certain amount of cetyltrimethylammonium bromide solution and the tetradecyl gemini surfactant solution are mixed to obtain the compound. The solvent is water and an organic solvent, and the organic solvent is an alcoholic solvent such as ethanol and methanol, a ketone solvent such as acetone. The preparation product may be in the form of a solution or dried as a solid powder.

The tetradecylglucose gemini surfactants and cetyltrimethylammonium bromide used in the present invention are all available compounds which are commercially available or can be prepared by the available method. The present invention is carried out at room temperature unless otherwise specified.

In the above production method, the molar ratio of the tetradecyl glucose gemini surfactant to cetyltrimethylammonium bromide is 3.5 to 4.5:1; as preferred, the tetradecyl glucose gemini surfactant to cetyltrimethylammonium bromide was 4:1. When the molar ratio is used, the prepared compound has better surface active properties and is about 10 times of the activity of the tetradecyl glucose gemini surfactant. In the present invention, cetyltrimethylammonium bromide itself has excellent properties such as osmotic, softening, emulsifying, antistatic, biodegradable and bactericidal properties.

The dodecyl glucose gemini surfactant compound and the tetradecyl glucose gemini surfactant compound of the present invention have characteristic high surface activity of gemini surfactants and are suitable for the separation and extraction of detergents and biofilm proteins. They also have non-toxic or low toxic and biodegradable property which are novel green biodegradable glycosyl gemini surfactants. The preparation method of the compound surfactant is simple and easy to be industrialized.

DETAILED DESCRIPTION OF THE PRESENT INVENTION

The detailed description of the present invention will now be described in further detail by the following examples, but the embodiments of the present invention are not limited thereto.

Example 1

Dodecyl glucose gemini surfactant (871.1 mg, 1 mmol) and tetradecyl trimethylammonium chloride (146.0 mg, 0.5 mmol) were dissolved in 100 mL of distilled water, and then the two solutions were mixed evenly, stirred at room temperature for 15 min and afforded the compound solution. The solution was freeze dried to obtain the compound as a white solid.
Surface Activity Test:
The critical micelle concentration (cmc) of the target product was determined as 0.0068 mmol/L at 20° C., which was 3 times higher than that of the compound dodecyl glucose gemini surfactant (cmc=0.02 mmol/L) and is suitable for separation and extraction of detergents and biofilm proteins.

Example 2

Dodecyl glucose gemini surfactant (871.1 mg, 1 mmol) and tetradecyl trimethylammonium chloride (146.0 mg, 0.5 mmol) were dissolved in 100 mL of ethanol, respectively, and the two solutions were mixed evenly, stirred at room temperature for 15 min and afforded the compound solution. The solution was freeze dried to obtain the compound as a white solid.

The structural identification and surface activity test data of the dodecyl glucose gemini surfactant prepared in this example are the same as in Example 1.

Example 3

Dodecyl glucose gemini surfactant (871.1 mg, 1 mmol) and tetradecyl trimethylammonium chloride (146.0 mg, 0.5 mmol) were dissolved in 100 mL of acetone, respectively, and the two solutions were mixed evenly, stirred at room temperature for 15 min and afforded the compound solution. The solution was freeze dried to obtain the compound as a white solid.

The structural identification and surface activity test data of the dodecyl glucose gemini surfactant prepared in this example were the same as in Example 1.

Example 4

Dodecyl glucose gemini surfactant (653.3 mg, 0.75 mmol) and tetradecyl trimethylammonium chloride (146.0 mg, 0.5 mmol) were dissolved in 100 mL of distilled water, respectively, and then the two solutions were mixed evenly, stirred at room temperature for 15 min and afforded the compound solution. The solution was freeze dried to obtain the compound as a white solid.
Surface Activity Test:
The critical micelle concentration (cmc) of the target product was determined as 0.0088 mmol/L at 20° C., which was 2 times higher than that of the compound dodecyl glucose gemini surfactant (cmc=0.02 mmol/L) and is suitable for separation and extraction of detergents and biofilm proteins.

Example 5

Dodecyl glucose gemini surfactant (1088.9 mg, 128 mmol) and tetradecyl trimethylammonium chloride (146.0 mg, 0.5 mmol) were dissolved in 100 mL of distilled water, and then the two solutions were mixed evenly, stirred at room temperature for 15 min and afforded the compound solution. The solution was freeze dried to obtain the compound as a white solid.
Surface Activity Test:
The critical micelle concentration (cmc) of the target product was 0.0085 mmol/L at 20° C., which was 2 times higher than that of the compound dodecyl glucose gemini surfactant (cmc=0.02 mmol/L) and is suitable for separation and extraction of detergents as well as biofilm proteins.

The reaction reagents used in Examples 1 to 5 were either commercially available or prepared by the available method in which the preparation method of the dodecyl gemini chains can be found in the literature (Liu, Songbai; Sang, Ruocheng; Hong, Shan; Cai, Yujing; Wang, Hua. "A Novel Type of Highly Effective Nonionic Gemini Alkyl O-Glucoside Surfactants: A Versatile Strategy of Design." Langmuir. 2013, 29, 8511-8516.).

Example 6

Tetradecyl glucose gemini surfactant (927.2 mg, 1 mmol) and cetyl trimethylammonium bromide (91.1 mg, 0.25 mmol) were dissolved in 100 mL of distilled water, respectively, and then the two solutions were homogeneously mixed and stirred at room temperature for 15 min to obtain the compound solution. The solution was freeze dried to obtain the compound as a white solid.
Surface Activity Test:
The critical micelle concentration (cmc) of the target product was 0.0054 mmol/L at 20° C., which was 10 times higher than that of the compound tetrahydrate glucose gemini surfactant (cmc=0.053 mmol/L) and is suitable for separation and extraction of detergents and biofilm proteins.

Example 7

Tetradecyl glucose gemini surfactant (927.2 mg, 1 mmol) and cetyl trimethylammonium bromide (91.1 mg, 0.25 mmol) were dissolved in 100 mL of ethanol, respectively, and then the two solution were homogeneously mixed and stirred at room temperature for 15 min to obtain the compound solution. The solution was freeze dried to obtain the compound as a white solid.

The structural identification and surface activity test data of the obtained tetradecyl glucose gemini surfactant in this example were the same as in Example 6.

Example 8

Tetradecyl glucose gemini surfactant (927.2 mg, 1 mmol) and cetyl trimethylammonium bromide (91.1 mg, 0.25 mmol) were dissolved in 100 mL of acetone, respectively. Then, the above prepared two solutions were homogeneously mixed and stirred at room temperature for 15 min to obtain the compound solution. The solution was freeze dried to obtain the compound as a white solid.

The structural identification and surface activity test data of the obtained tetradecyl glucose gemini surfactant in this example were the same as in Example 6.

Example 9

Tetradecyl glucose gemini surfactant (1043.1 mg, 1.125 mmol) and cetyl trimethylammonium bromide (91.1 mg, 0.25 mmol) were dissolved in 100 mL of distilled water, respectively, and the above prepared two solutions were homogeneously mixed and stirred at room temperature for 15 min to obtain the compound solution. The solution was freeze dried to obtain the compound as a white solid.

Surface Activity Test:

The critical micelle concentration (cmc) of the target product was determined to be 0.0105 mmol/L by the platinum plate method at 20° C., which was 5 times higher than that of the mixture of cetyl glucose gemini surfactant (cmc=0.053 mmol/L) and is suitable for separation and extraction of detergents and biofilm proteins.

Example 10

Tetradecyl glucose gemini surfactant (811.3 mg, 0.875 mmol) and cetyl trimethylammonium bromide (91.1 mg, 0.25 mmol) were dissolved in 100 mL of distilled water, respectively, and then the two solutions were homogeneously mixed and stirred at room temperature for 15 min to obtain the compound solution. The solution was freeze dried to obtain the compound as a white solid.

Surface Activity Test:

The critical micelle concentration (cmc) of the target product was determined as 0.0088 mmol/L by platinum plate method at 20° C., which was 6 times higher than that of the mixture of cetyl glucose gemini surfactant (cmc=0.053 mmol/L) and is suitable for separation and extraction of detergents and biofilm proteins.

The reagents used in Examples 6 to 10 were commercially available or prepared by the available method. The preparation method of the tetradecyl glucose chain can be found in the literature (Liu, Songbai; Sang, Ruocheng; Hong, Shan; Cai, Yujing; Wang, Hua. "A Novel Type of Highly Effective Nonionic Gemini Alkyl O-Glucoside Surfactants: A Versatile Strategy of Design." Langmuir. 2013, 29, 8511-8516.)

The invention claimed is:

1. A glucose gemini surfactant compound comprising a dodecyl glucose gemini surfactant and tetradecyltrimethylammonium chloride; or a tetradecyl glucose gemini surfactant and cetyltrimethylammonium bromide; wherein the structure of the dodecyl glucose gemini surfactant is as follows:

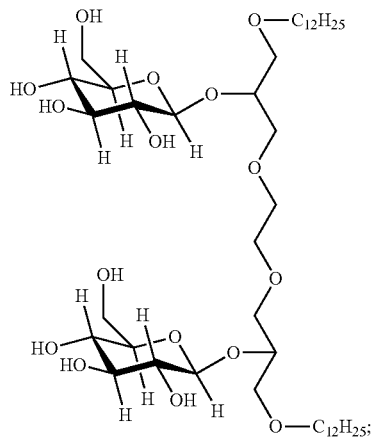

the structure of the tetradecyl glucose gemini surfactant is as follows:

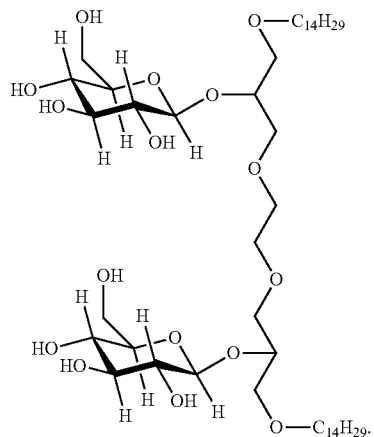

2. The glucose gemini surfactant compound according to claim 1, characterized in that the molar ratio of dodecyl glucose gemini surfactant to tetradecyltrimethylammonium chloride is 1.5-2.5:1.

3. The glucose gemini surfactant compound according to claim 1, characterized in that the molar ratio of dodecyl glucose gemini surfactant to tetradecyltrimethylammonium chloride is 2:1.

4. The glucose gemini surfactant compound according to claim 1, wherein the dodecyl glucose gemini surfactant compound is a solid.

5. The glucose gemini surfactant compound according to claim 1, wherein the dodecyl glucose gemini surfactant compound is a solution in which the solvent is one or a combination of water, ethanol, methanol, acetone.

6. The glucose gemini surfactant compound according to claim 1, characterized in that the molar ratio of tetradecyl glucose gemini surfactant to cetyltrimethylammonium bromide is 3.5-4.5:1.

7. The glucose gemini surfactant compound according to claim 1, characterized in that the molar ratio of tetradecyl glucose gemini surfactant to cetyltrimethylammonium bromide is 4:1.

8. The glucose gemini surfactant compound according to claim 1, wherein the tetradecyl glucose gemini surfactant compound is a solid.

9. The glucose gemini surfactant compound according to claim 1, characterized in that the tetradecylglucose gemini surfactant compound is a solution in which the solvent is one or a combination of water, methanol, ethanol, acetone.

10. A process for the preparation of a glucose gemini surfactant compound comprising: dissolving dodecyl glucose gemini surfactant with tetradecyltrimethylammonium chloride, or tetradecyl glucose gemini surfactant and cetyltrimethylammonium bromide in a solvent, mixing evenly to obtain the compound.

* * * * *